(12) United States Patent
Rolando et al.

(10) Patent No.: US 9,186,249 B2
(45) Date of Patent: Nov. 17, 2015

(54) VALVE PROSTHESIS AND KIT

(71) Applicant: Sorin Group Italia S.r.l., Milan (IT)

(72) Inventors: Giovanni Rolando, Chivasso (IT);
Paolo Gaschino, Castagneto Po (IT);
Laura Ghione, Turin (IT); Andrea Marchisio, Ivrea (IT); Monica Achiluzzi, Chivasso (IT)

(73) Assignee: Sorin Group Italia S.r.l., Milan (IT)

( * ) Notice: Subject to any disclaimer, the term of this patent is extended or adjusted under 35 U.S.C. 154(b) by 48 days.

(21) Appl. No.: 13/962,789

(22) Filed: Aug. 8, 2013

(65) Prior Publication Data

US 2014/0046434 A1 Feb. 13, 2014

(30) Foreign Application Priority Data

Aug. 10, 2012 (EP) .................................... 12425139

(51) Int. Cl.
*A61F 2/24* (2006.01)
(52) U.S. Cl.
CPC ............. *A61F 2/2412* (2013.01); *A61F 2/2418* (2013.01); *A61F 2/2436* (2013.01); *A61F 2220/0075* (2013.01)
(58) Field of Classification Search
CPC ... A61F 2/2412; A61F 2/2418; A61F 2/2445; A61F 2220/0008; A61F 2220/0016
USPC ........... 623/1.11–1.12, 1.23–1.24, 1.26, 2.11, 623/2.15, 2.18–2.19, 2.36–2.37
See application file for complete search history.

(56) References Cited

U.S. PATENT DOCUMENTS

| 5,855,601 A | 1/1999 | Bessler et al. |
| 6,287,339 B1 | 9/2001 | Vazquez et al. |
| 6,312,465 B1 | 11/2001 | Griffin et al. |
| 6,425,916 B1 | 7/2002 | Garrison et al. |
| 6,458,153 B1 | 10/2002 | Bailey et al. |

(Continued)

FOREIGN PATENT DOCUMENTS

| EP | 0133420 B1 | 2/1988 |
| EP | 0155245 B1 | 5/1990 |

(Continued)

OTHER PUBLICATIONS

European Search Report issued in EP Application No. 12425060, completed Jun. 27, 2012, 7 pages.

(Continued)

*Primary Examiner* — Todd Manahan
*Assistant Examiner* — Charles Wei
(74) *Attorney, Agent, or Firm* — Faegre Baker Daniels LLP (57) ABSTRACT

Described is a valve prosthesis comprising: an annular structure, and a plurality of valve leaflets, and a plurality of anchoring members attached around the annular structure, the anchoring members including: a web portion coupled to the annular structure and extending axially thereto, and two end portions at axially opposed sides of the web portion, the end portions having: an insertion condition for insertion of the prosthesis, wherein the end portions are aligned to the web portion and extend axially with respect to the annular structure; and an anchoring condition for anchoring the prosthesis, wherein the end portions extend at an angle to the web portion radially outwardly of the annular structure to provide anchoring of the prosthesis proximally and distally, respectively, of the annulus, and wherein one end portion forms an obtuse angle with the web portion.

20 Claims, 7 Drawing Sheets

(56) References Cited

U.S. PATENT DOCUMENTS

| | | |
|---|---|---|
| 6,461,366 B1 | 10/2002 | Seguin |
| 6,530,952 B2 | 3/2003 | Vesely |
| 6,569,196 B1 | 5/2003 | Vesely |
| 6,629,534 B1 | 10/2003 | St. Goar et al. |
| 6,821,297 B2 | 11/2004 | Snyders |
| 6,974,476 B2 | 12/2005 | McGuckin, Jr. et al. |
| 7,011,681 B2 | 3/2006 | Vesely |
| 7,018,406 B2 | 3/2006 | Seguin et al. |
| 7,018,408 B2 | 3/2006 | Bailey et al. |
| 7,252,682 B2 | 8/2007 | Seguin |
| 7,329,278 B2 | 2/2008 | Seguin et al. |
| 7,381,220 B2 | 6/2008 | Macoviak et al. |
| 7,556,646 B2* | 7/2009 | Yang et al. ............... 623/2.11 |
| 7,585,321 B2 | 9/2009 | Cribier |
| 7,648,528 B2 | 1/2010 | Styrc |
| 7,708,775 B2 | 5/2010 | Rowe et al. |
| 7,717,955 B2 | 5/2010 | Lane et al. |
| 7,753,949 B2 | 7/2010 | Lamphere et al. |
| 7,758,640 B2 | 7/2010 | Vesely |
| 7,776,083 B2 | 8/2010 | Vesely |
| 7,806,927 B2 | 10/2010 | Styrc |
| 7,892,281 B2 | 2/2011 | Seguin et al. |
| 7,959,672 B2 | 6/2011 | Salahieh et al. |
| 8,016,882 B2 | 9/2011 | Macoviak et al. |
| 8,025,695 B2 | 9/2011 | Fogarty et al. |
| 8,048,153 B2 | 11/2011 | Salahieh et al. |
| 8,070,802 B2 | 12/2011 | Lamphere et al. |
| 8,105,375 B2 | 1/2012 | Navia et al. |
| 8,167,935 B2 | 5/2012 | McGuckin, Jr. et al. |
| 8,221,493 B2 | 7/2012 | Boyle et al. |
| 8,236,049 B2 | 8/2012 | Rowe et al. |
| 8,287,591 B2 | 10/2012 | Keidar et al. |
| 8,323,335 B2 | 12/2012 | Rowe et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,449,599 B2 | 5/2013 | Chau et al. |
| 8,454,686 B2 | 6/2013 | Alkhatib |
| 8,540,767 B2 | 9/2013 | Zhang |
| 8,579,964 B2 | 11/2013 | Lane et al. |
| 8,579,966 B2 | 11/2013 | Seguin et al. |
| 8,597,348 B2 | 12/2013 | Rowe et al. |
| 2005/0137691 A1 | 6/2005 | Salahieh et al. |
| 2006/0195183 A1 | 8/2006 | Navia et al. |
| 2007/0043435 A1* | 2/2007 | Seguin et al. ............. 623/2.11 |
| 2008/0140189 A1 | 6/2008 | Nguyen et al. |
| 2008/0208327 A1 | 8/2008 | Rowe |
| 2009/0125098 A1 | 5/2009 | Chuter |
| 2009/0248149 A1 | 10/2009 | Gabbay |
| 2009/0276040 A1 | 11/2009 | Rowe et al. |
| 2010/0004739 A1 | 1/2010 | Vesely |
| 2010/0145440 A1 | 6/2010 | Keranen |
| 2010/0174363 A1 | 7/2010 | Castro |
| 2010/0256741 A1 | 10/2010 | Hansen |
| 2010/0312333 A1* | 12/2010 | Navia et al. ............... 623/2.36 |
| 2011/0029072 A1 | 2/2011 | Gabbay |
| 2011/0098800 A1 | 4/2011 | Braido et al. |
| 2011/0137397 A1 | 6/2011 | Chau et al. |
| 2011/0166636 A1 | 7/2011 | Rowe |
| 2011/0178597 A9 | 7/2011 | Navia et al. |
| 2011/0218620 A1 | 9/2011 | Meiri et al. |
| 2011/0224785 A1* | 9/2011 | Hacohen ................... 623/2.18 |
| 2011/0313515 A1 | 12/2011 | Quadri et al. |
| 2012/0010697 A1 | 1/2012 | Shin et al. |
| 2012/0016464 A1 | 1/2012 | Seguin |
| 2012/0022640 A1 | 1/2012 | Gross et al. |
| 2012/0046742 A1 | 2/2012 | Tuval et al. |
| 2012/0078353 A1 | 3/2012 | Quadri et al. |
| 2012/0078360 A1* | 3/2012 | Rafiee ........................ 623/2.37 |
| 2012/0101571 A1 | 4/2012 | Thambar et al. |
| 2012/0165930 A1 | 6/2012 | Gifford, III et al. |
| 2012/0303116 A1* | 11/2012 | Gorman et al. ............. 623/2.11 |
| 2013/0018449 A1 | 1/2013 | Bailey et al. |
| 2013/0035759 A1 | 2/2013 | Gross et al. |
| 2013/0053950 A1 | 2/2013 | Rowe et al. |
| 2013/0144381 A1 | 6/2013 | Quadri et al. |
| 2013/0211508 A1 | 8/2013 | Lane et al. |
| 2013/0245753 A1 | 9/2013 | Alkhatib |
| 2013/0253643 A1 | 9/2013 | Rolando et al. |

FOREIGN PATENT DOCUMENTS

| | | |
|---|---|---|
| EP | 0515324 B1 | 12/1996 |
| EP | 1233731 B1 | 11/1999 |
| EP | 1049425 B1 | 11/2000 |
| EP | 1176913 B1 | 2/2002 |
| EP | 1251803 B1 | 10/2002 |
| EP | 1335683 B1 | 8/2003 |
| EP | 1343438 B1 | 9/2003 |
| EP | 1401359 B1 | 3/2004 |
| EP | 1408850 B1 | 4/2004 |
| EP | 1562522 B1 | 8/2005 |
| EP | 1621162 B1 | 2/2006 |
| EP | 1701668 B1 | 9/2006 |
| EP | 1758523 B1 | 3/2007 |
| EP | 1935378 A1 | 6/2008 |
| EP | 1690515 B1 | 7/2008 |
| EP | 2000115 B1 | 12/2008 |
| EP | 2072027 A1 | 6/2009 |
| EP | 2078498 B1 | 7/2009 |
| EP | 2138132 B1 | 12/2009 |
| EP | 2250976 A1 | 11/2010 |
| EP | 2258312 B1 | 12/2010 |
| EP | 2260796 B1 | 12/2010 |
| EP | 2260797 B1 | 12/2010 |
| EP | 2260798 B1 | 12/2010 |
| EP | 2340075 B1 | 7/2011 |
| EP | 2641569 A1 | 3/2012 |
| EP | 2476394 B1 | 7/2012 |
| EP | 2486893 A1 | 8/2012 |
| EP | 2526895 B1 | 11/2012 |
| EP | 2526898 B1 | 11/2012 |
| EP | 2526899 B1 | 11/2012 |
| EP | 2529696 B1 | 12/2012 |
| EP | 2529697 B1 | 12/2012 |
| EP | 2529698 B1 | 12/2012 |
| EP | 2529699 B1 | 12/2012 |
| EP | 2537487 B1 | 12/2012 |
| WO | WO2008091515 A2 | 7/2008 |
| WO | WO2011044994 A1 | 4/2011 |
| WO | WO2012063228 A1 | 5/2012 |
| WO | WO2013037805 A1 | 3/2013 |
| WO | WO2013075215 A1 | 5/2013 |
| WO | WO2013082454 A1 | 6/2013 |
| WO | WO2013096541 A1 | 6/2013 |

OTHER PUBLICATIONS

European Search Report issued in EP Application No. 12425139, completed Jan. 16, 2013, 7 pages.

European Search Report issued in EP Application No. 13425113, mailed Feb. 7, 2014, 6 pages.

International Search Report issued in PCT/IB2013/052090, mailed Jul. 21, 2013, 4 pages.

International Search Report issued in PCT/IB2014/063176, mailed Oct. 9, 2014, 12 pages.

* cited by examiner

VALVE PROSTHESIS AND KIT

CROSS-REFERENCE TO RELATED APPLICATION

This application claims priority to European Application No. 12425139.8, filed Aug. 10, 2012, which is herein incorporated by reference in its entirety.

TECHNICAL FIELD

This invention relates to valve prostheses. Valve prostheses may be used to functionally replace a native heart (e.g., atrioventricular) valve. In particular, such a valve may be used as a, e.g., mitral or tricuspid prosthesis that allows sutureless implantation by a minimally invasive approach.

BACKGROUND

Various valve pathologies, such as, in the case of cardiac valve pathologies, mitral valve pathologies (essentially stenosis or insufficiency), can be surgically treated either with "repair" techniques or with "replacement" techniques.

Some physicians consider repair techniques to provide a higher life expectancy and less morbidity as compared to replacement techniques. This may be related to the conservation of native valve structures, e.g., leaflets and chordae tendineae, in the repair process. Various valve pathologies may thus benefit from the availability of arrangements permitting valve replacement (such as, e.g., Mitral Valve Replacement or "MVR") while also conserving the native valve structures.

SUMMARY

Various embodiments may provide a valve prosthesis that can be implanted without removing the native valve leaflets and/or the native chordae tendineae.

Various embodiments may provide a collapsible valve prosthesis.

In various embodiments, a valve prosthesis may include sutureless anchoring members. In various embodiments, such anchoring members may be designed to anchor to the native valve site (e.g., the mitral annulus and leaflets) without appreciable radial expansion of the implant site.

In various embodiments, a valve prosthesis may include an annular structure (e.g., cylindrical) that is open or closed, and adapted to define a blood flow lumen having an inflow side and an outflow side and to support therein one or more prosthetic valve leaflets. The annular structure may be provided with a set of anchoring members attached (i.e., mounted) therearound for coupling the prosthesis to the natural valve site (e.g., the annulus, leaflets, chordae tendineae).

In various embodiments, the prosthetic valve leaflets may include biological tissue (optionally of a "dry tissue" type) and/or polymer.

In various embodiments, the prosthesis may be deployed at an implant site, e.g., by means of a sliding sleeve delivery system and a balloon to expand the prosthesis to match the implant site dimensions.

Various embodiments may thus include, among other features, an Embodiment 1: A valve prosthesis for location at a valve annulus, the prosthesis including: an annular structure with an axial blood flow lumen and at least one valve leaflet movable under the action of blood between an open position and a closed position to permit and to impede, respectively, blood flow through said axial blood flow lumen, and a plurality of anchoring members attached around the annular structure, the anchoring members including: a web portion coupled to the annular structure and extending axially thereto, and two end portions at axially opposed sides of the web portion, wherein the end portions admit (that is, are adapted to assume, e.g., by moving to and/or being brought to): a) an insertion condition for insertion of the prosthesis, wherein the end portions are aligned to the web portion and extend axially with respect to the annular structure; b) an anchoring condition for anchoring the prosthesis, wherein the end portions extend at an angle to the web portion radially outwardly of the annular structure to provide anchoring of the prosthesis proximally and distally, respectively, of the annulus.

Embodiment 2. The valve prosthesis of Embodiment 1, including anchoring members having at least one end portion with an insertion condition wherein the at least one end portion is spread apart from the web portion and extends axially from the annular structure and an anchoring condition wherein the at least one end portion is folded towards the web portion at an angle thereto radially outwardly of the annular structure.

Embodiment 3: The valve prosthesis of Embodiment 1 or Embodiment 2, including anchoring members having at least one end portion with an insertion condition wherein the at least one end portion is folded against the web portion and extends axially with respect to the annular structure and an anchoring condition wherein the at least one end portion is deployed away from the web portion at an angle thereto radially outwardly of the annular structure.

Embodiment 4: The valve prosthesis of any of the previous Embodiments including a sheet-like covering on the outer side of the annular structure and anchoring members having their web and end portions radially outwardly of the covering.

Embodiment 5: The valve prosthesis of any of the previous Embodiments including anchoring members adjustably coupled to the annular structure.

Embodiment 6: The valve prosthesis of any of the previous Embodiments including anchoring members coupled to the annular structure by flexible links.

Embodiment 7: The valve prosthesis of Embodiment 4 and Embodiment 6, wherein the flexible links include suture stitches through the sheet-like covering.

Embodiment 8: The valve prosthesis of any of the previous Embodiments, wherein the anchoring members include an elastic, preferably super-elastic, material.

Embodiment 9: The valve prosthesis of any of the previous Embodiments, including anchoring members including one of: an elongated ring-shaped body having loop portions and an intermediate portion between the loop portions forming the end portions and the web portion, respectively, of the anchoring member, a blade-like body.

Embodiment 10: The valve prosthesis of any of the previous Embodiments, including anchoring members distributed with uniform spacing around the annular structure.

Embodiment 11: The valve prosthesis of any of Embodiments 1 to 9, including anchoring members distributed with non-uniform spacing around the annular structure.

Embodiment 12: The valve prosthesis of any of the previous claims, including a set of identical anchoring members.

Embodiment 13: The valve prosthesis of any of Embodiments 1 to 11, including anchoring members having different sizes and/or shapes at different places around the annular structure.

Embodiment 14: The valve prosthesis of any of the previous Embodiments, wherein the annular structure has a shape selected from circular, non-circular, D-shaped.

Embodiment 15: The valve prosthesis of any of the previous Embodiments, including anchoring members with end portions which elastically assume the anchoring condition in the absence of applied deformation stress.

Embodiment 16: The valve prosthesis of any of the previous Embodiments, wherein the annular structure is contractible to a radially contracted insertion condition and expandable to a radially expanded implantation condition.

Embodiment 17: The valve prosthesis of Embodiment 16, wherein the annular structure is self-expandable to a radially expanded implantation condition.

Embodiment 18: The valve prosthesis of Embodiment 15 or Embodiment 16, wherein the annular structure is expandable to a radially expanded implantation condition under the action of an expansion member.

Embodiment 19: A delivery kit for a valve prosthesis including: an unexpanded expandable member carrying a valve according to any of Embodiments 1 to 18 radially contracted thereon, a sheath member arranged around the expandable member and radially constricting to the insertion condition the end portions of the anchoring members of the valve prosthesis radially contracted on the expandable member, the sheath member slidable over the expandable member to sequentially disengage the end portions of the anchoring members and permit the end portions to assume the anchoring condition with the annular structure radially expanded due to expansion of the expandable member.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

Various embodiments will now be described, purely by way of non-limiting example, with reference to the annexed figures, wherein:

FIGS. 5 and 6, each including two portions designated a) and b), respectively, show details of embodiments;

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the following description, numerous specific details are given to provide a thorough understanding of various exemplary embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings and reference signs provided herein are for convenience only and do not interpret the scope or meaning of the embodiments.

In the figures, reference number 1 designates a valve prosthesis such as a cardiac valve prosthesis (in brief, "cardiac valve"). In various embodiments, the valve prosthesis 1 may be of a type adapted to be implanted by adopting a "sutureless" approach, e.g., via non-invasive thoracic (micro)surgery or via a percutaneous procedure.

In various embodiments, the valve prosthesis 1 may be a collapsible valve prosthesis.

Various embodiments may apply to valve prostheses for use in contexts different from cardiac or arterial: use in peripheral vessels, possibly venous, are exemplary of such different contexts.

The general operating principles of such prostheses and the related design and implantation criteria (including details of implementation of strictly technological nature, such as, e.g., choice and treatment of the materials, etc.) are known in the art, which makes it unnecessary to provide a detailed description of such principles and criteria.

In the exemplary embodiments considered herein, the prosthesis 1 may include: an annular (e.g., cylindrical) structure including a support structure or armature 2 and a set of leaflets 3 applied on the armature 2 and including one or more (e.g., three) valve leaflets 3a, 3b, 3c, and a plurality of anchoring members 10 distributed around the annular structure 2, 3.

As used herein, the term "cylindrical" may refer to a structure having a generally cylindrical shape without however requiring a structure having a constant diameter/cross section along its length and/or a structure which is circular in cross section; various embodiments may include, e.g., a non-circular cross section, such as, e.g., a D-shape.

Exemplary techniques for forming valve leaflets and applying them on an armature such as the armature 2 which may be adapted for use in various embodiments are described, for example, in EP 0 133 420 A1, EP 0 155 245 A1 and EP 0 515 324 A1, each of which are incorporated herein by reference, the last document cited referring to the construction of a cardiac valve prosthesis of biological tissue of the type commonly referred to as "stentless".

Figure 1:
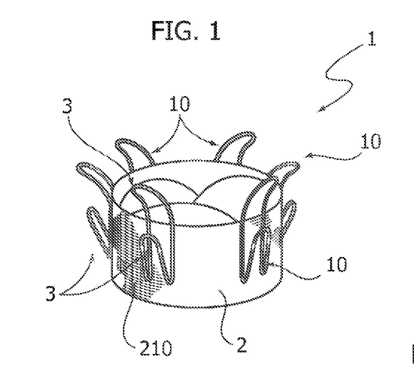
FIG. 1 is a perspective view of a valve prosthesis.
Figure 2:
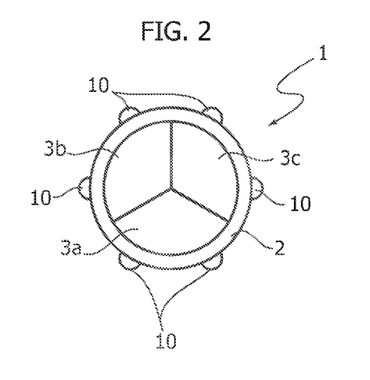
FIGS. 2 to 4 are schematic views of embodiments.

In various embodiments, the valve leaflet(s) may include a base portion with an overall annular pattern designed to extend from the portion of the valve 1 which, with the prosthesis implanted, is at an "inflow" position, i.e., a position "fluidodynamically" proximal with respect to the direction of flow of blood through the prosthesis (from above downwards, as viewed, e.g., in FIG. 1).

In various embodiments, starting from such a base portion, pleated or cusp formations may extend in an axial direction in the structure of the prosthesis 1. In various embodiments, plural valve leaflets (e.g., three valve leaflets 3a, 3b and 3c, as shown) may extend between pairs of cusp formations adjacent to one another.

In various embodiments, different criteria, known in the art, may be adopted to construct the leaflet(s) of the prosthesis 1.

In the exemplary embodiments considered herein, the prosthesis 1 may be a valve prosthesis for use as a prosthetic mitral valve, i.e., as a valve permitting blood flow from the left atrium (inflow side) into the left ventricle (outflow side) during diastole while preventing backflow from the left ventricle into the left atrium as the left ventricle contracts during systole to pump blood into the aorta towards the circulatory system.

In various embodiments, each leaflet (e.g., 3a, 3b and 3c) may exhibit: a fluidodynamically proximal (i.e., "inflow") edge with an arched pattern, which extend from a base formation between adjacent pleat formation, and a fluidodynamically distal (i.e., "outflow") edge which extends toward the central orifices of the prosthesis 1 so as to be able to co-operate with, e.g., the homologous edges of the other valve leaflets.

The valve leaflet or leaflets (e.g., 3a, 3b, 3c) are able to undergo deformation, divaricating and moving up against the armature 2 (i.e., in an open position of the valve) so as to enable free flow of the blood through the valve prosthesis 1 from an inflow to an outflow side of the blood flow lumen.

When the pressure gradient, and hence the directional flow, of the blood flow through the prosthesis tends to be reversed, the valve leaflet or leaflets then move into the closed position of the valve (e.g., a radially co-apting position of the valve leaflets) in which the leaflet or leaflets prevent the flow of the blood through the prosthesis 1 in the opposite direction: undesired flow of blood through the valve prosthesis 1 from an outflow to an inflow side of the valve prosthesis 1 and the natural valve site is thus impeded.

In various embodiments, the valve leaflet or leaflets may be made in such a way as to assume spontaneously, in the absence of external stresses, the closed position/configuration represented in FIGS. 1 to 4.

While various embodiments described herein will at least implicitly refer by way of non-limiting example to mitral valve replacement (MVR) in conjunction with conserving the native valve leaflets and, possibly, the native chordae tendineae, various embodiments may also be used in conjunction with replacement of other cardiac valves.

Various embodiments may thus engage the native anatomical features in various ways. In various embodiments, the anchoring members may contact one or more of the annular tissue, the leaflets, and the chordae tendineae.

In various embodiments, the "armature" portion 2 of the annular structure intended to extend into the native annulus through the native valve site to define a blood flow lumen therein may be configured to support the prosthetic valve leaflet(s), e.g., 3a, 3b, 3c in the blood flow lumen and may be provided with anchoring members 10 attached around the annular structure 2, 3 for coupling with the natural valve site.

Various embodiments may provide anchoring members having a first end portion engaging the inflow portion (e.g., upper or atrial, in the exemplary case of mitral placement) of the annulus and a second end portion engaging (e.g., grasping) the outflow portion (e.g., lower or ventricular, in the exemplary case of mitral placement).

In various embodiments, the prosthesis 1 may be of a collapsible type and the armature 2 of the annular structure may have a radially contractible-extendable annular pattern of e.g. wire-like members or struts. Such a pattern may include a stent-like structure or one or more annular members (circular, elliptical or with more complex shapes, e.g., a D-shape) connected by longitudinal connection members or links.

Apertures may be provided in one or more of these struts (e.g., in one or more of the links) to permit the set of leaflets 3 to be applied onto the armature 2, e.g., via stitching.

In various embodiments, the armature 2 carrying the leaflet or leaflets 3 may be totally or partially covered (e.g., wrapped) with a sheet or tunic 210 of a biocompatible material, e.g. of the type accepted for use in suture rings for heart valves or in vascular grafts. In various embodiments, such a sheet-like member may include biocompatible fabric (e.g., Dacron® or other polymers) and/or a biological tissue.

In various embodiments, the covering 210 may be on the outer side of the annular structure 2, 3, e.g., as schematically shown in FIG. 1, and optionally also on the inner side of the armature 2 of the annular structure (e.g., between the armature 2 and the leaflet or leaflets 3).

In various embodiments, the covering (outer and/or inner to the armature 2) may be of annular shape, open or closed. In various embodiments, the covering may be of a shorter length (i.e., "height") than the annular structure 2, 3, thus leaving uncovered at least one end (e.g., outflow) of the annular structure 2, 3.

In various embodiments, the prosthesis 1 may thus include a sheet-like covering applied onto the annular structure to totally or partially cover the annular structure.

In various embodiments, the covering 210 (or the portion of the covering 210) arranged on the outer side of the annular structure 2,3 may act as a separation member between the armature 2 and the anchoring members 10 and may thus provide one or more of following functions: avoiding transfer of excessive mechanical loads/stresses between the between the armature 2 and the anchoring members 10, optionally avoiding undesired effects (e.g., induced corrosion in a saline medium such as blood) if the armature 2 and the anchoring members 10 include different materials (e.g., balloon expandable and self-expandable), making the location of the anchoring members 10 with respect to the armature 2 adjustable e.g. to allow a slight adjustment of the position of attachment (e.g., circumferential) to the armature 2.

In various embodiments, the covering 210 may also be functional in impeding undesired peri-valvular blood flow (i.e., leakage) around the prosthesis.

In various embodiments, the anchoring members 10 may be coupled to the annular portion 2, 3, e.g., by links or struts, optionally flexible.

In various embodiments, the anchoring members 10 may be arranged with their portions 10a, 10b, and 10c (to be described in the following) lying radially outwardly of the covering 210 which covers the outer side of the annular portion 2, 3.

FIGS. 1 to 4 are exemplary of the possibility of providing any number N (N≥2), e.g., three, four, five, six or more anchoring members 10 distributed around the annular structure 2.

In various embodiments, the anchoring members 10 may be angularly distributed around the prosthesis 1.

Figure 3:
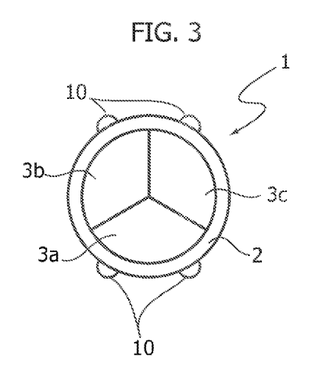
Figure 4:
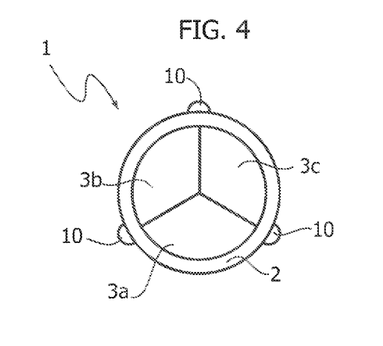

Angular distribution may be either uniform (as in the exemplary embodiments of FIGS. 1, 2 and 4) or non-uniform (as schematically represented in FIG. 3).

In various embodiments, a uniform angular distribution of the anchoring members 10 may be optionally adopted with an annular structure which (e.g., in a radially expanded implantation condition of the prosthesis 1) has a substantially round shape.

In various embodiments, a non-uniform angular distribution of the anchoring members 10 may be optionally adopted with an annular structure which (e.g., in a radially expanded implantation condition of the prosthesis) may be non-circular, e.g. D-shaped. In various embodiments, such a D-shape may be adopted for mitral implantation (e.g., MVR) to more closely reproduce the shape of the natural valve annulus.

In various embodiments, the anchoring members 10 may be attached to the armature 2 by being produced as a single piece (e.g., same material) with the armature 2 with, e.g., links or "bridges" extending between the armature 2 and the anchoring members 10.

In various embodiments, the anchoring members 10 may be attached to the armature 2 as independent elements.

In various embodiments, the anchoring members 10 may be coupled to the armature 2 in such a way as to allow, e.g., a slight adjustment of the position of attachment (e.g., circumferential) to the armature 2.

As further described before, the anchoring members 10 are designed to be functional in anchoring the armature 2 (and the valve leaflet or leaflets 3 applied thereon) at the implantation site by preventing the prosthesis 1 from being displaced under the action of blood and heart pulsation while the native valve leaflets and possibly the native chordae tendineae may be retained.

While the instant description refers by way of example to a prosthesis 1 for use at a mitral position, various embodiments may be adapted for use as a valve prosthesis for location at a different location (e.g., aortic, tricuspid).

FIGS. 5 and 6 are exemplary views of embodiments of an anchoring member 10 adapted to be distributed around the annular structure 2, 3 of the prosthesis as exemplified in FIGS. 1 to 4.

Figure 5A:
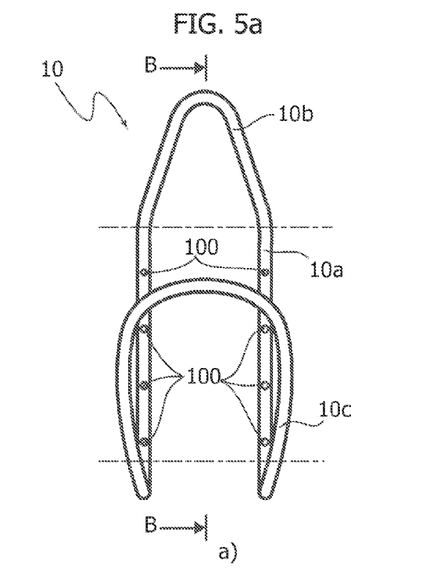
Figure 6A:
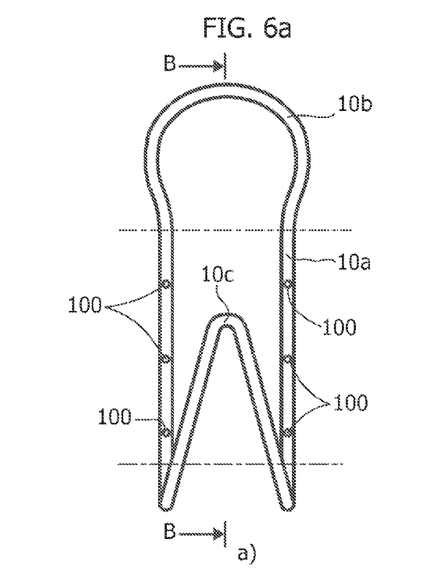

FIGS. 5a and 6a, are "front" views of an anchoring member 10, i.e., an anchoring member 10 as notionally seen when observed from a viewpoint external to the prosthesis 1 looking radially inwardly towards the prosthesis 1.

Figure 5B:
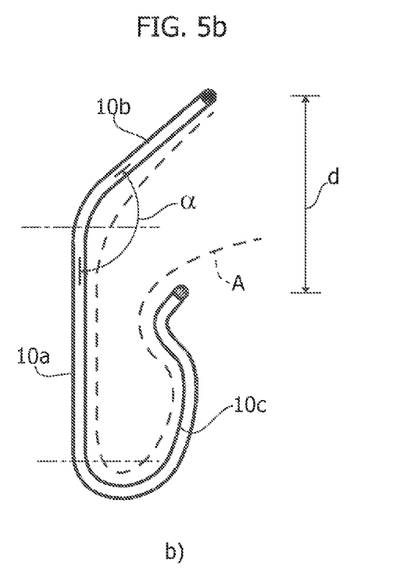
Figure 6B:
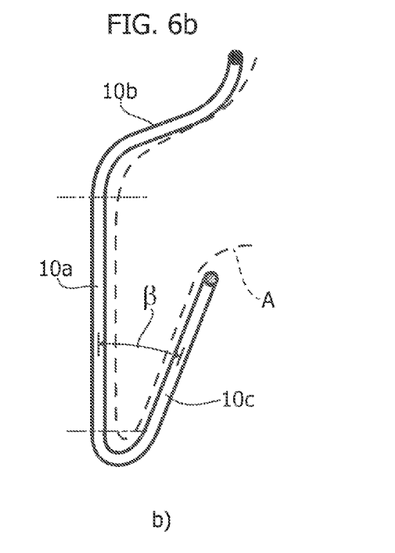

FIGS. 5b and 6b, are "lateral" views of an anchoring member 10, i.e., an anchoring member 10 as notionally seen in a diametrical plane to the prosthesis 1 approximately corresponding to a cross sectional plane along the line B-B in each of FIGS. 5a and 6a.

In both FIGS. 5b and 6b, a schematic representation A is provided in phantom line of natural tissues at the annular site (e.g., annulus proper, natural valve leaflets, chordae tendineae and so on) which in various embodiments are not removed and are thus "embraced" or "grasped" by the anchoring member 10.

The anchoring members 10 are thus functional in anchoring the prosthesis 1 at the implantation site A by preventing the prosthesis 1 from being displaced under the action of blood and heart pulsation.

FIGS. 5 to 22 refer to possible implantation in a condition where the direction of free blood flow through the prosthesis 1 is from above downwards so that, in all of FIGS. 5 to 22 the "top" side is "inflow" or "fluidodynamically proximal", while the "bottom" side is "outflow" or "fluidodynamically distal".

In various embodiments, the anchoring members 10 distributed around the annular structure 10 may include: a central web portion 10a intended to be coupled with the annular structure 2, 3 of the prosthesis 1 and extending axially thereto, a first end portions 10b (inflow or proximal, in the exemplary embodiment shown), and a second end portion 10c (outflow or distal, in the exemplary embodiment shown).

Figure 11:
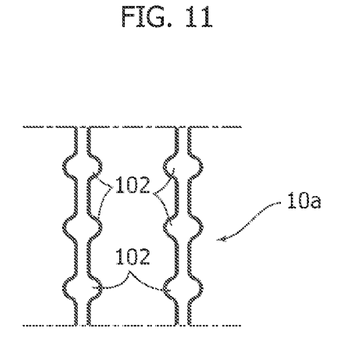

In various embodiments, the anchoring members 10 may include an elongated ring or loop whose end loops define the end portions 10b and 10c, while the intermediate branches connecting the end loops of the ring define the web portion 10a (see, e.g., FIG. 11 or a representation of such a web portion 10a alone).

In various embodiments, the anchoring members 10 may include a blade-like body.

In various embodiments (irrespective of whether provided in the form of an elongate ring body or in a different shape, e.g., as a blade-like member), the anchoring members 10 may be elastic bodies which, in the absence of applied deformation stress, may assume an un-deformed "rest" shape in the form of a C-shape or G-shape (i.e., channel like) as exemplified in FIGS. 5b) and 6b).

In various embodiments, the anchoring members 10 may include a super(elastic) material, Ni—Ti materials such as Nitinol™ being exemplary of such superelastic materials.

In various embodiments, as further detailed in the following in connection with FIG. 22a, the anchoring members 10 being elastically deformable may permit to extend the end portions 10b, 10c to an "open", extended shape wherein the end portions 10b, 10c are spread apart (i.e., stretched out) from the web portion 10a to extend axially outwardly from the annular structure 2, 3 of the prosthesis substantially aligned with the web portion 10a.

In various embodiments, as further detailed in the following in connection with FIG. 22b, the anchoring members 10 being elastically deformable may permit to urge at least one of the end portions (e.g., end portion 10c) to lie against the web portion 10a being substantially aligned therewith.

Figure 27:
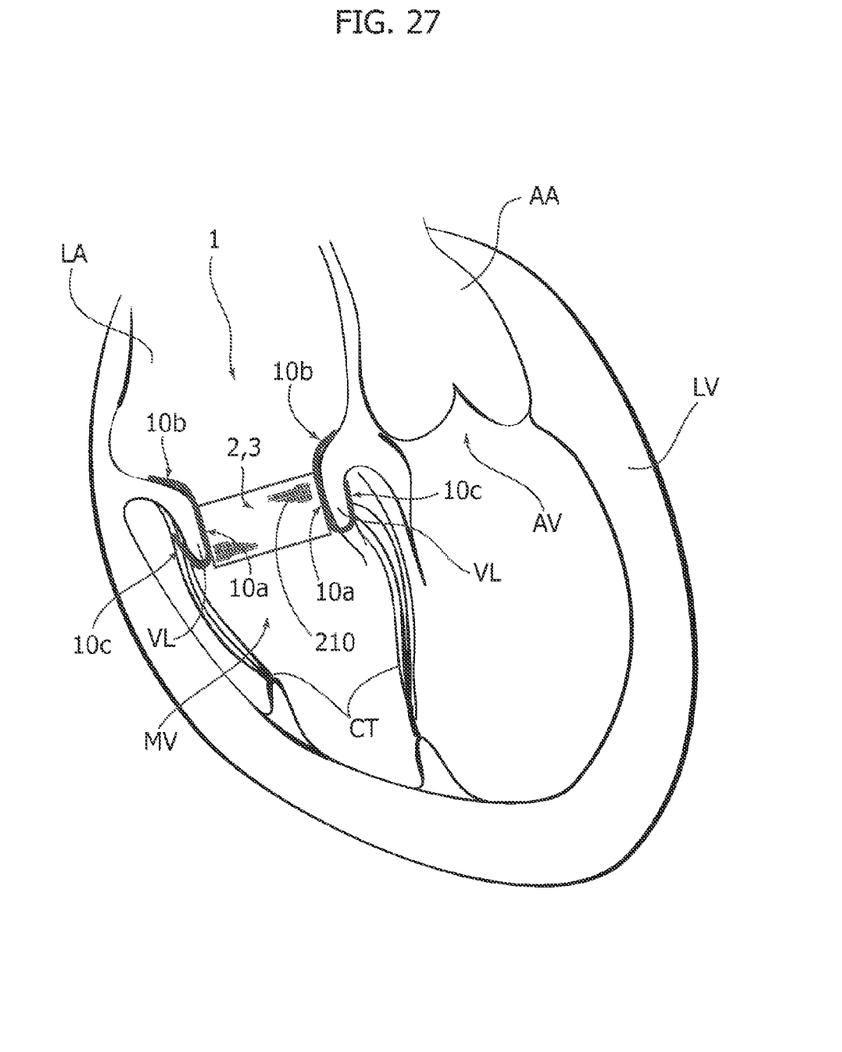
FIG. 27 is representative of a mitral application of a valve prosthesis.

Whatever the means adopted to deform the end portion(s) 10b, 10c in alignment to the web portion 10a, in various embodiments, once the deformation stress is removed, the anchoring members 10 will elastically return to an overall C-shape or G-shape as shown for example in FIGS. 5 and 6, namely the "anchoring" condition of the prosthesis 1 where the end portions 10b, 10c are at an angle to the web portion 10a and may thus grasp proximally and distally the annulus region A to secure the prosthesis 1 at the implantation site the annular site tissue A as schematically depicted, e.g., in FIGS. 5b and 6b and 27.

Those of skill in the art will appreciate that elastic flexibility due to, e.g., super elasticity, is just one of the exemplary manners of achieving the described anchoring mechanism.

For instance, in various embodiments, an anchoring mechanism as represented for example in FIGS. 5b and 6b may be achieved in a number of ways including (but not limited) to either or both the end portions 10b, 10c reaching a closed "anchoring" condition (FIGS. 5 to 10, 13 to 22 and 25, 26 to be described later) as a result of a shape-memory effect triggered, e.g., by heat or electro-magnetic waves applied to the prosthesis.

In various embodiments, an anchoring mechanism as described may be achieved with either or both the end portions 10b, 10c being hinged to the web portion 10a.

Previous references to a G-shape (see, e.g., FIG. 5) in addition to a C-shape (see, e.g., FIG. 6) in the closed condition of the anchoring members 10 describe the end portions 10b, 10c as being adapted to be both symmetrical and non-symmetrical with respect to the web portion 10a.

In various embodiments, this may apply both to the (radially) frontal view profile as exemplified in FIGS. 5a and 6a, FIGS. 7-8 and 13-15 and to the diametrical cross-sectional profile as exemplified in FIGS. 5b, 6b, 9-10 and 16-22.

Figure 12:
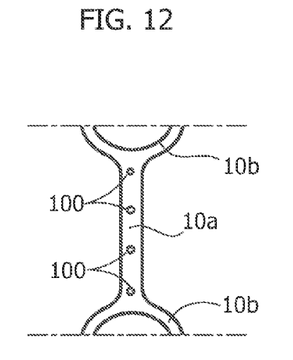

In FIGS. 7-10 and 13-22, FIGS. 7-10 refer to the first (herein inflow or proximal) end portion 10b while FIGS. 13 to 22 refer to the second (herein outflow or distal) end portion 10a. FIGS. 11 and 12 refer to exemplary embodiments of the central portion 10a therebetween.

In various embodiments, when in the anchoring condition, the first end portion 10b, may form to the central web portion 10a an angle α (alpha—see FIG. 5b) which is an obtuse angle (namely between 90° and 180°). In various embodiments, such an angle may be 120-145°.

In various embodiments, when in the anchoring condition, the second end portion 10c, may form to the central web portion 10a an acute angle β (beta—see FIG. 6b) (namely less than 90°).

In various embodiments, when in the anchoring condition, the second end portion 10c may form together with the web portion 10a a sort of hook, lock or clamp adapted to "embrace" or "grasp" the annular site A, e.g., at the fluidodynamically distal side of the annular orifice.

Such an effect is functional in ensuring that the anchoring members 10 (and thus the annular structure 2, 3 of the prosthesis 1 to which the anchoring members 10 are coupled) are securely retained at the implantation site and may prevent the prosthesis 1 from being displaced under the action of blood and heart pulsation, especially when the prosthesis impedes undesired distal-to-proximal backflow of blood.

In various embodiments, such a result may be achieved while the native valve leaflets and, possibly, the chordae tendineae are retained.

In various embodiments, the anchoring mechanism just described may take advantage of the fact that the valve leaflets and, possibly, the native chordae tendineae are retained as may be the case in MVR: the prosthesis may be safely retained in place due the end portions 10c forming together with the central portions 10a "hooks" adapted to capture the natural annular tissues A (see, e.g., FIGS. 5b and 6b).

In the case of MVR, the anchoring mechanism just described may also take advantage of the fact that the native chordae tendineae, being retained (if still extant and functional), are in a position to transfer onto the cardiac wall from which they extend at least part of the force induced by blood pressure onto the prosthetic leaflet(s) as they did in the case of the natural valve being replaced by the prosthesis.

In various embodiments, due to the angular distribution of the anchoring members 10 around the prosthesis 1, the end portions 10b, when oriented at an angle to the web portion 10a in the anchoring condition, may jointly form an extraannular structure adapted to extend collar-like and to (axially) rest over the annulus (i.e., supra-annularly) of the natural valve site, e.g., (in the case of mitral placement) at the inflow side of the blood flow lumen through the prosthesis 1.

The anchoring mechanism just described essentially acts upon both sides of the annulus (i.e., both proximally and distally of the annulus A), with the anchoring members exerting a force primarily axially—rather than radially—upon the annulus.

In various embodiments, undesired radial expansion of the annulus (which may be already weakened in the case of, e.g., MVR) may be avoided while ensuring that the prosthesis is securely retained at the implantation site, without risks of displacement.

In various embodiments, asymmetrical shaping of the end portions 10b and 10c with respect to the central portion 10a may ensure an anchoring/retaining action of the valve prosthesis 1 at the implantation site which matches in a complementary manner the anatomy of the annular site, which is generally convex at the inflow side, with unremoved natural leaflets spread open by the prosthesis 1 and extending from the annulus at the outflow side.

In various embodiments, the "axial" anchoring mechanism just described makes it possible to adopt for the annular structure 2,3 shapes other than circular, i.e., non-circular such as elliptic, oval, eye-shaped or D-shaped (which may closely match the overall D-shape of the natural mitral annulus).

Such an anchoring mechanism as exemplified may be functional in minimizing interaction of a prosthetic mitral valve as exemplified herein with adjacent heart districts, e.g., the Left Ventricular Outflow Tract or LVOT.

In various embodiments, the anchoring members 10 may be all identical.

In various embodiments, the anchoring members 10 may not be all identical.

In various embodiments, the anchoring members 10 may have different sizes (e.g., lengths) and/or shapes at different places of the contour of the prosthesis 1 in order to match the local characteristics of the nature annulus at different angular positions.

In various embodiments, irrespective of whether identical or non-identical, the anchoring members 10 may have different orientations of the end portions 10b, 10c at different places of the contour of the prosthesis 1 in order to match the local characteristics of the natural annulus at different angular positions.

The figures describe exemplary embodiments where the distal ends of the end portions 10b, 10c portions, when at an angle to the web portion 10a in the anchoring condition of the prosthesis 1, are at a distance to each other (see "d" in FIG. 6b).

In various embodiments, irrespective of whether identical or non-identical, the anchoring members 10 may have different values of the distance d at different places of the contour of the prosthesis 1. In various embodiments this may permit to match the local characteristics of the natural annulus, e.g., in order to "grasp" the natural tissues to a greater or smaller extent at different angular positions of the prosthesis 1.

In various embodiments, in one of more of the anchoring members 10 the distance d may be zero or even become "negative," i.e., with the end portions 10b and 10c meshing with each other in the anchoring condition of the prosthesis 1.

Figure 7:
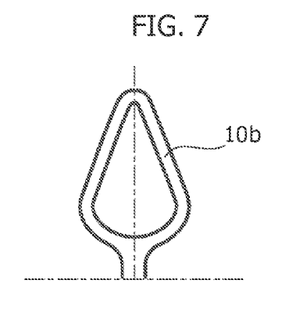
FIGS. 7 to 21, 22a and 22b show various details of embodiments.
Figure 8:
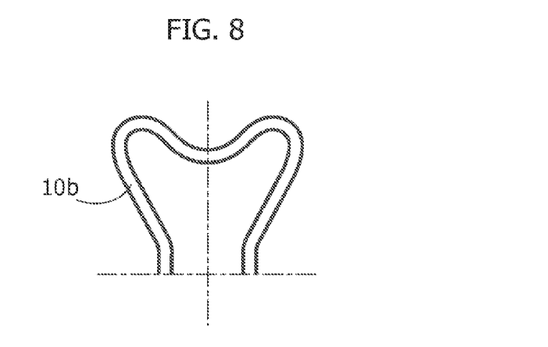
Figure 9:
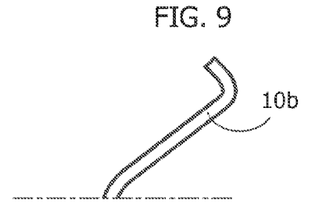
Figure 10:
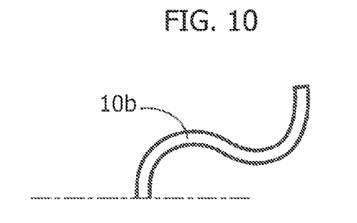
Figure 13:
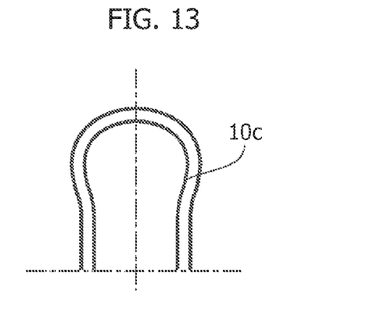
Figure 14:
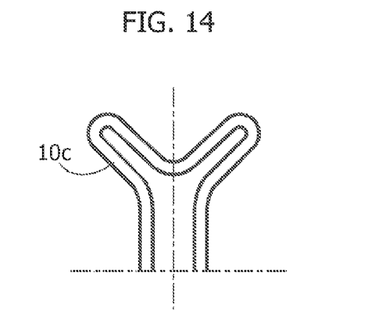
Figure 15:
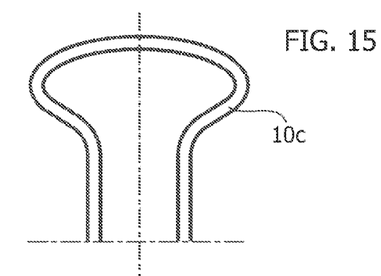
Figure 16:
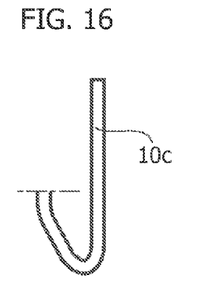
Figure 17:
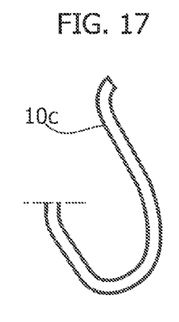
Figure 18:
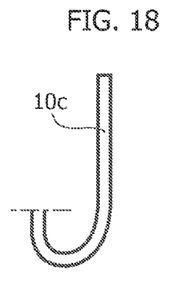
Figure 19:
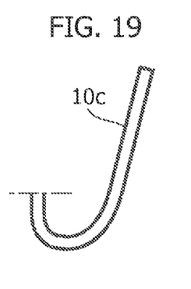
Figure 20:
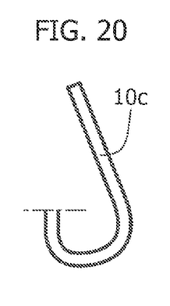
Figure 21:
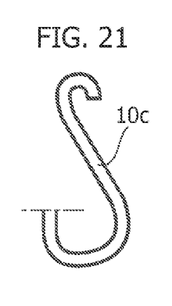

The figures exemplify a number of different possible shapes/orientations for the end portions 10b and 10c in the anchoring members 10 (assumed to be shown in the closed "anchoring" position). For instance: FIGS. 5a, 5b: end portion 10b approximately triangular, bent at approximately 135° to the direction of the web portion 10a; end portion 10c approximately round, bent at approximately 30° to the direction of the web portion 10a with a terminal hook-like "tip" portion bent outwardly of the prosthesis 1; FIGS. 6a, 6b: end portion 10b approximately round, again bent at approximately 135° to the direction of the web portion 10a with a S-shaped cross profile thus having a terminal "tip" portion oriented axially of the prosthesis 1; end portion 10c approximately triangular bent at approximately 30° to the direction of the web portion 10a; FIG. 7: end portion 10b approximately spade-like, with an open (hollow) center; FIG. 8: end portion 10b approximately fishtail shaped, again with an open (hollow) center; FIG. 9: end portion 10b at approximately 135° to the web portion 10a with a S terminal "tip" portion bent inwardly of the prosthesis 1; FIG. 10: end portion 10b at approximately 90° to the web portion 10a with an S-shape overall with a terminal hook-like "tip" portion bent axially of the prosthesis 1; FIG. 13: end portion 10c approximately round; FIG. 14: end portion 10c approximately fishtail shaped with an open (hollow) center; FIG. 15: end portion 10c approximately mushroom-shaped with an open (hollow) center; FIG. 16: end portion 10c hook-like having a root portion bent outwardly of the prosthesis and a terminal portion at 0° to the web portion 14a (i.e., extending axially of the prosthesis 1; FIG. 17: end portion 10c again hook-like with a root portion bent outwardly of the prosthesis and a S-shaped terminal portion again extending axially of the prosthesis 1 with a tip bent outwardly of the prosthesis 1; FIG. 18: end portion 10c hook-like having a half-circular root portion bent outwardly of the prosthesis and a terminal portion at 0° to the web portion 14a (i.e., extending axially of the prosthesis); FIG. 19: end portion 10c hook-like having a half-circular root portion bent outwardly of the prosthesis and a terminal portion at about 30° to the web portion 14a; FIG. 20: end portion 10c once again hook-like with a half-circular root portion bent outwardly of the prosthesis and a terminal portion at about −30° to the web portion 14a (i.e., bent inwardly of the prosthesis 1); and FIG. 21: end portion 10c once again hook-like with a half-circular root portion bent outwardly of the prosthesis and a terminal portion at about −30° to the web portion 14a (i.e., bent inwardly of the prosthesis 1) with a lock-like tip bent outwardly of the prosthesis 1.

Figure 22A:
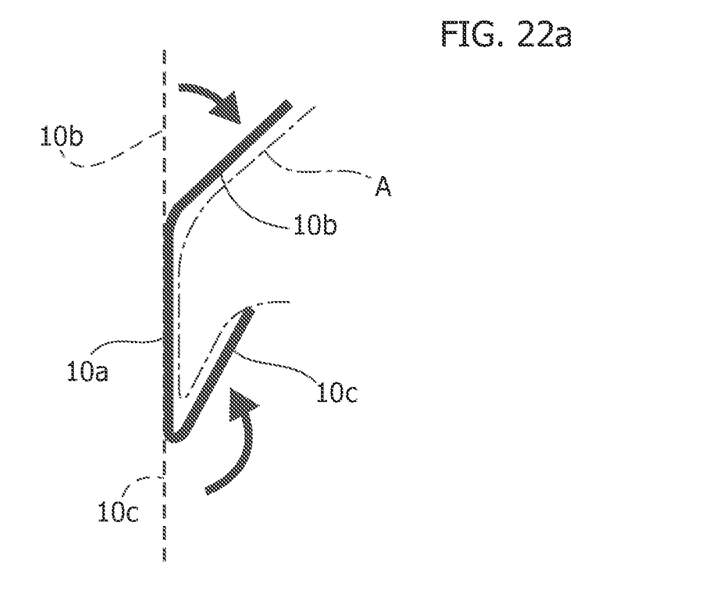

FIG. 22a is exemplary of embodiments where the end portions 10b, 10c are extendable to an insertion condition of the prosthesis wherein the end portions 10b, 10c are aligned with the web portion 10a by being spread apart to extend axially away from the web portion 10a as depicted in broken lines in FIG. 22a to extend axially and away from the annular structure 2, 3.

As schematically indicated by the arrows in FIG. 22a, the end portions 10b, 10c are then re-closable (e.g., elastically) to an anchoring condition (depicted in full lines), wherein the end portions 10b, 10c are bent or folded towards the web portion 10a (and thus at an angle therewith) radially outwardly from the annular structure to provide anchoring of the prosthesis proximally and distally of the annulus A (schematically represented in chain lines).

Figure 22B:
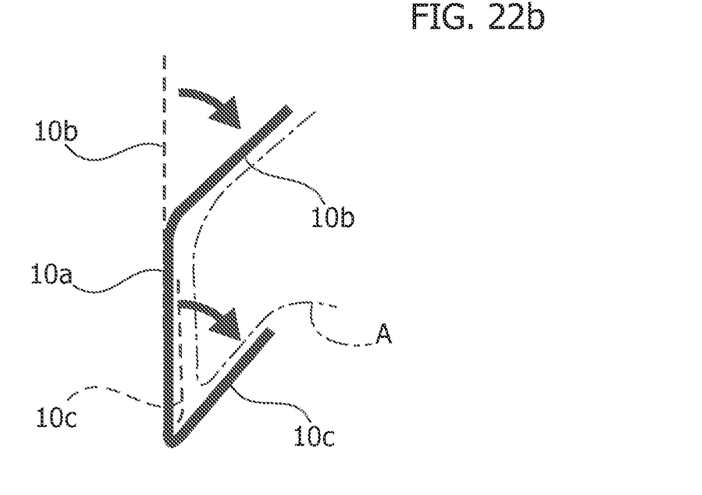

FIG. 22b is representative of exemplary embodiments wherein the end portion 10b may be again extendable to an insertion condition of the prosthesis wherein the end portion 10b is spread apart to extend axially away from the web portion 10a and is thus aligned with the web portion 10a. In the exemplary embodiments to which FIG. 22c refers, alignment of the end portion 10c with the web portion 10a to an insertion condition of the prosthesis is achieved by the end portion being fully folded towards (e.g., urged against) the web portion 10a. As schematically indicated by the arrows in FIG. 22b, the end portions 10b, 10c may then move (e.g., elastically) to an anchoring condition with the end portion 10b again re-closing towards the web portion 10a, while the end portion 10c deploys (i.e., opens up) away from the web portion 10a to reach the anchoring condition depicted in full lines in FIG. 22b where the end portions 10b, 10c are again at angle to the web portion 10a radially outwardly of the annular structure 2, 3 to again provide anchoring of the prosthesis proximally and distally of the annulus A.

In various embodiments, the deployment mechanism exemplified in FIG. 22b for the end portion 10c may be applied (also) to the end portion 10b. FIGS. 22a and 22b describe two exemplary ways of having end portions 10b, 10c located at axially opposed sides of the web portion 10a, with the end portions 10b, 10c that admit (that is, are adapted to assume, e.g., by moving to and/or being brought to): a) an insertion condition (for insertion of the prosthesis 1 at the implantation site) wherein the end portions 10b, 10c are aligned to the web portion 10a and extend axially with respect to the annular structure 2, 3; b) an anchoring condition (for anchoring the prosthesis 1 at the implantation site), wherein the end portions 10b, 10c extend at an angle to the web portion 10a (see e.g. α=alpha and β=beta in FIGS. 5b and 6b) radially outwardly from the annular structure 2, 3 to provide anchoring of the prosthesis proximally and distally, respectively, of the annulus A.

FIG. 22a is exemplary of anchoring members 10 having one or both (i.e., at least one) end portions 10b, 10c with: an insertion condition wherein the end portion(s) 10b, 10c are spread apart (i.e., fully opened) away from the web portion 10a and extend axially from the opposite sides of the annular structure 2, 3 (outwardly thereof), and an anchoring condition wherein the end portion(s) 10b, 10c are folded (i.e., re-closed) towards the web portion 10a at an angle thereto radially outwardly of the annular structure 2, 3.

FIG. 22b is exemplary of anchoring members 10 having (at least) one end portion—e.g., end portion 10c—with: an insertion condition wherein the end portion 10c is folded against the web portion 10a and extends axially with respect to (and axially inwardly of) the annular structure 2, 3, and an anchoring condition wherein the at least one end portion 10c is deployed away from the web portion 10a at an angle thereto radially outwardly of the annular structure 2, 3.

Both mechanisms exemplified in FIGS. 22a and 22b may be applied to anchoring members 100 obtained from ring or loop body of a wire-like material as discussed in the foregoing and to blade-like anchoring members produced as cutouts from a sheet of—e.g., (super)elastic material.

In various embodiments, the anchoring members 10 may be formed in such a way that the anchoring condition (i.e., the condition wherein the end portions 10b, 10c are at an angle to the web portion 10a radially outwardly from the annular structure 2,3) is an unconstrained "rest" condition to which the anchoring members 10 elastically return in the absence of deformation stress applied to the anchoring members.

In the exemplary embodiments of FIGS. 5 and 6, the intermediate portions 10a includes two rectilinear branches of the intermediate portion of the elongated ring-shaped body constituting the anchoring member 10. FIGS. 11 and 12 represent other possible exemplary embodiments of the central web portion 10a.

As already described, in various embodiments, the covering 210 (or the portion of the covering 210) arranged on the outer side of the annular structure 2,3 may act as a separation member between the armature 2 and the anchoring members 10 coupled therewith with the portions 10a, 10b, and 10c arranged to lie radially outwardly of the covering 210.

In various embodiments, the anchoring members 10 may be coupled to the annular portion 2, 3 by various types of links, optionally flexible.

In various exemplary embodiments, the central portion 10a of the anchoring members 10 may be "stitched" to the (e.g., textile) covering 210 of the armature 2.

In various exemplary embodiments, the central portion 10a of the anchoring members 10 may be provided with holes 100 for possible use in coupling the relative anchoring member 10 to the annular structure 2, 3, e.g., by using a wire member (e.g., a suture) through the (e.g., textile) covering 210 of the armature 2 (see FIG. 1).

Such coupling by stitches may permit the anchoring members 10 to be adjustably coupled to the structure 2, 3. During implantation the physician may moderately adjust the location of the members 10 with respect to the structure before securing suture.

No such holes may be provided in various embodiments as exemplified in FIG. 11, wherein the branches of the intermediate web portion 10a are provided with enlarged zones 102 which may be exploited, e.g., for stitching the anchoring member 10 to the covering 210 of the armature 2.

Holes 100 adapted for passing suture for adjustably coupling the anchoring member 10 to the covering 210 of the armature 2, 3 are exemplified also in the embodiment of FIG. 12: there the intermediate portion 10a is simply comprised of the rectilinear bar or "link" connecting to end portions 10b, 10c which may possibly have the shape as depicted in FIG. 12.

Those of skill in the art will promptly appreciate that any of the shapes/orientations exemplified for the parts 10a, 10b and 10c of the anchoring members 10 in any of figures may be freely combined with any another in any possible combination in order to meet specific requirements.

A collapsible valve prosthesis 1 as exemplified herein can be deployed at the implant site (e.g., mitral) by resorting to sutureless (e.g., thoracic microsurgery or percutaneous) techniques.

As schematically shown in FIGS. 23 to 26, delivery and deployment may be by means of delivery system including an expandable member such as an expandable balloon B and a sliding sleeve delivery feature S. Such delivery system may be configured for a single access root, e.g., atrial as schematically exemplified, or for different access roots, e.g., ventricular (transapical).

Documents such as EP 1 935 377 A1, EP 1 935 378 A1, EP 2 033 581 A1, EP 2 033 597 A1, EP 2 250 976 and EP applications 114425029.3 and 12425060.6, each of which are hereby incorporated by reference, are exemplary of various concepts adapted to be embodied in such delivery system.

In various embodiments, the anchoring members 10 may be self-expandable (e.g., include shape-memory material such as Ni—Ti or Nitinol™, harmonic steel, polymers) so that in the absence of applied deformation stress the end portions 10b, 10c will elastically assume the anchoring condition.

In various embodiments, the annular structure 2, 3 may include materials (e.g., stainless steel, chrome-cobalt alloys, titanium) making it expandable to a radially expanded implantation condition from a radially contracted insertion condition under the action of an expansion member, e.g., be balloon-expandable.

In various embodiments the annular structure 2, 3 may be self-expandable.

Figure 23:
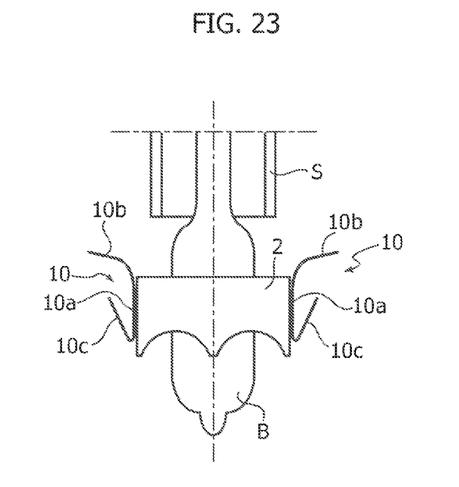
FIGS. 23 to 26 are schematically representative of implantation of a valve prosthesis.
Figure 24:
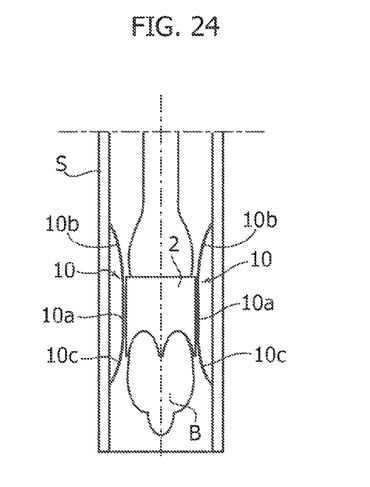

FIG. 23 schematically represents a collapsible valve prosthesis 1 including an annular structure 2, 3 in a radially expanded condition having the anchoring members 10 arranged therearound in their C-shaped or G-shaped "closed" condition.

The (unexpanded) balloon B may be inserted into the axial lumen of the annular structure 2, 3 and the annular structure 2, 3 is then "crimped" (i.e., radially contracted, by known means) onto the balloon B, while the anchoring members 10 are brought to the insertion condition wherein the end portions 10b, 10c are aligned with the web portion 10a.

As exemplified in FIG. 24a, this may occur, e.g., by "stretching" the end portions 10b, 10c to their extended condition wherein the end portions 10b, 10c are spread apart from the web portion 10a and extend substantially axially of the annular structure 2, 3 outwardly of the axially opposed ends of the structure 2, 3.

This may apply to embodiments adopting the mechanism described with reference to FIG. 22a.

In embodiments adopting the mechanism described with reference to FIG. 22b, the end portions 10b may again be stretched to their extended condition wherein they are spread apart from the web portion 10a, while the end portions 10c may be bent inwardly against the web portion 10a, so that both end portions 10b and 10c extend substantially axially of the annular structure 2.

Whatever the solution adopted for bringing the end portions 10b, 10c to the insertion condition wherein they are aligned with the web portion 10a, the sleeve feature S may then be located (e.g., by axial sliding) around the prosthesis 1 in such a way to constrict and thus retain the anchoring members 10 to the insertion condition with the end portions 10b, 10c of the anchoring members 10 aligned with the web portion 10a.

The sleeve feature S may also similarly constrict and retain to the radially contracted condition the structure 2, 3 in case this is self-expandable.

The arrangement of parts just described may correspond to various embodiments of an implantation kit permitting the prosthesis 2 to be advanced to the implantation location (e.g. via a single access route, e.g., atrial).

Figure 25:
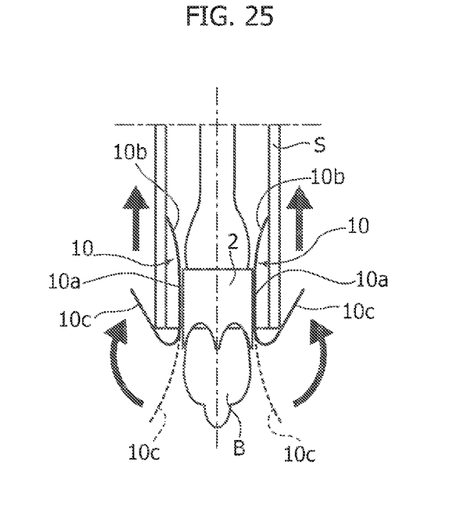
Figure 26:
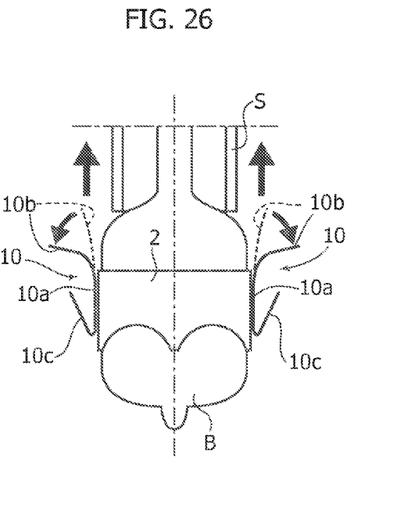

Once the desired implantation location is (at least approximately) reached, the sleeve S may be retracted proximally to uncover the end portions 10c of the anchoring members (see, e.g., FIG. 25). Being no longer radially constricted by the sleeve S, the end portions 10c (herein assumed to be elastic) will return to their original unconstricted condition wherein they are at an angle (see, e.g., R, beta in FIG. 6b) to the web portion 10a. That is, the end portions 10c will rotate towards (FIG. 22a) or away (FIG. 22b) the web portion 10a to reach a configuration as exemplified previously wherein the end portions 10c "embrace" or "grasp" one of the sides (distal, namely outflow in the exemplary mitral environment considered herein) of the native valve site.

This may enable the practitioner to refine positioning of the prosthesis 1 by causing the re-closed end portions 10b to "capture" the natural tissue structures at the outflow side of the native valve site.

Axial proximal retraction of the sleeve S may continue thus releasing the opposed end portions 10b of the anchoring members 10. The end portions 10b (herein assumed to be elastic) will return to their original unconstricted condition wherein they are at an angle (see, e.g., α, alpha in FIG. 5b) to the web portion 10a. That is, the end portions 10c will rotate with respect to the web portion 10a to reach a configuration wherein the end portions 10b complete the C-shape or G-shape (i.e., channel-like) of the anchoring members 10 while, by actuating the expandable balloon B, the practitioner will be in a position to produce the radial expansion of the annular structure carrying the valve leaflet or leaflets 3.

The end portions 10b will abut against the (herein "inflow") side of the native annulus by completing engagement of the natural valve site to provide secure anchoring of the prosthesis 1 at the desired implantation site without exerting undue radial expansion force of the annulus site.

In various embodiments, balloon expandability of the annular structure 2, 3 may permit to coordinate radial expansion from the radially contracted crimped condition, while releasing the prosthesis 1 by deflating the balloon B (only) when the desired implant condition is achieved.

FIG. 27 is a schematic representation of the left ventricle LV of a human heart with a mitral valve MV controlling the flow of blood from the left atrium LA into the left ventricle LV and an aortic valve AV controlling the flow of blood pumped from the left ventricle VL into the aorta AA.

FIG. 27 is a schematic representation of the application of an embodiment for Mitral Valve Replacement (MVR) with at least substantial conservation of the structures of the native mitral valve ("MV"), namely the mitral valve leaflets ("VL") and chordae tendineae ("CT").

As shown in FIG. 27, for the exemplary case of mitral valve placement, once expanded from a contracted condition to an expanded condition for anchoring at the annulus of the natural valve site MV, the prosthesis 1 will have a final geometrical shape which will generally approximate the physiological shape and dimension of the mitral annulus.

In such an exemplary embodiment, the annular portion 2, 3 will define a blood flow lumen having an inflow (i.e., atrial) side and an outflow (i.e., ventricular) side, with the armature 2 supporting the prosthetic valve leaflet or leaflets 3a, 3b, 3c in the blood flow lumen, while the anchoring members 10 will couple with the natural valve site by capturing the native tissues, primarily the natural valve leaflets VL without exerting undue radial expansion force of the annulus site.

Also, the chordae tendineae CT (if present, i.e., if extant and not removed) will still co-operate in retaining the prosthesis 1 at the implantation site resisting displacement by ventricular-to-atrial blood back pressure (e.g., during systole): this may be due to the chordae tendineae CT being "grasped" at their ends by the end portions 10c and/or due to the chordae tendineae CT being still connected to the natural valve leaflets VL which are in turn "grasped" by the end portions 10c.

Of course, without prejudice to the underlying principle of the invention, the details of construction and the embodiments may vary widely with respect to what is described and illustrated herein by way of example, without thereby departing from the extent of protection, the extent of protection being determined by the annexed claims.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A valve prosthesis for location at a valve annulus, the prosthesis comprising:
    an annular structure with an axial blood flow lumen and a plurality of valve leaflets movable under the action of blood between an open position and a closed position to permit and to impede, respectively, blood flow through said axial blood flow lumen, and
    a plurality of anchoring members attached around the annular structure, the anchoring members including:
        a web portion coupled to the annular structure and extending axially thereto, the web portion having at least one width, and
        two end portions at axially opposed sides of the web portion, the end portions having: at least one width, an insertion condition for insertion of the prosthesis, wherein the end portions are aligned to the web portion and extend axially with respect to the annular structure; and an anchoring condition for anchoring the prosthesis, wherein the end portions are shaped asymmetrically and wherein a width of at least one end portion differs from a width of the web portion and extend at an angle to the web portion radially outwardly of the annular structure to provide anchoring of the prosthesis proximally and distally, respectively, of the annulus, and wherein one end portion forms an obtuse angle with the web portion.

2. The valve prosthesis of claim 1, wherein the end portions can assume an insertion condition wherein each end portion is spread apart from the web portion and extends axially from the annular structure and an anchoring condition wherein each end portion is folded towards the web portion at an angle thereto radially outwardly of the annular structure.

3. The valve prosthesis of claim 1, wherein the end portions can assume an insertion condition wherein each end portion is folded against the web portion and extends axially with respect to the annular structure and an anchoring condition wherein each end portion is deployed away from the web portion at an angle thereto radially outwardly of the annular structure.

4. The valve prosthesis of claim 1, including a sheet-like covering on the outer side of the annular structure and anchoring members having their web and end portions radially outwardly of the covering.

5. The valve prosthesis of claim 1, wherein the anchoring members are coupled to the annular structure by flexible links.

6. The valve prosthesis of claim 1, wherein the anchoring are members adjustably coupled to the annular structure.

7. The valve prosthesis of claim 5, wherein the flexible links include suture stitches through the sheet-like covering.

8. The valve prosthesis of claim 1, wherein the anchoring members include an elastic material.

9. The valve prosthesis of claim 1, including anchoring members having a body shape selected from a group consisting of:
    an elongated ring-shaped body having loop portions and an intermediate portion between the loop portions forming the end portions and the web portion, respectively, of the anchoring member, and
    a blade-like body.

10. The valve prosthesis of claim 1, wherein the anchoring members are distributed with uniform spacing around the annular structure.

11. The valve prosthesis of claim 1, wherein the anchoring members are distributed with non-uniform spacing around the annular structure.

12. The valve prosthesis of claim 1, including a set of identical anchoring members.

13. The valve prosthesis of claim 1, the anchoring members having different sizes and/or shapes at different places around the annular structure.

14. The valve prosthesis of claim 1, wherein the annular structure has a shape selected from a group consisting of circular, non-circular, and D-shaped.

15. The valve prosthesis of any of claim 1, anchoring members including end portions which elastically assume the anchoring condition in the absence of applied deformation stress.

16. The valve prosthesis of claim 15, wherein the annular structure is expandable to a radially expanded implantation condition under the action of an expansion member.

17. The valve prosthesis of claim 1, wherein the annular structure is contractible to a radially contracted insertion condition and expandable to a radially expanded implantation condition.

18. The valve prosthesis of claim 17, wherein the annular structure is self-expandable to the radially expanded implantation condition.

19. A delivery kit for a valve prosthesis including:
    an unexpanded expandable member carrying a valve radially contracted thereon, wherein the valve comprises:
        an annular structure with an axial blood flow lumen and a plurality of valve leaflets movable under the action of blood between an open position and a closed position to permit and to impede, respectively, blood flow through said axial blood flow lumen, and a plurality of anchoring members attached around the annular structure, the anchoring members including:

a web portion coupled to the annular structure and extending axially thereto, the web portion having at least one width, and two end portions at axially opposed sides of the web portion, the end portions having: at least one width, an insertion condition for insertion of the prosthesis, wherein the end portions are aligned to the web portion and extend axially with respect to the annular structure; and an anchoring condition for anchoring the prosthesis, wherein the end portions are shaped asymmetrically and wherein a width of at least one end portion differs from a width of the web portion and extend at an angle to the web portion radially outwardly of the annular structure to provide anchoring of the prosthesis proximally and distally, respectively, of the annulus, and wherein one end portion forms an obtuse angle with the web portion; and a sheath member arranged around the expandable member and radially constricting to the insertion condition, the end portions of the anchoring members of the valve prosthesis radially contracted on the expandable member, the sheath member slidable over the expandable member to sequentially disengage the end portions of the anchoring members to permit the end portions to assume the anchoring condition with the annular structure radially expanded due to expansion of the expandable member.

20. A method of implanting a valve prosthesis at a valve annulus, comprising the steps of:

providing a delivery sleeve;

providing a valve prosthesis within the delivery sleeve, wherein the valve prosthesis comprises:

an annular structure with an axial blood flow lumen and a plurality of valve leaflets movable under the action of blood between an open position and a closed position to permit and to impede, respectively, blood flow through said axial blood flow lumen, and a plurality of anchoring members attached around the annular structure, the anchoring members including:

a web portion coupled to the annular structure and extending axially thereto, the web portion having at least one width, and two end portions at axially opposed sides of the web portion, the end portions having: at least one width, an insertion condition for insertion of the prosthesis, wherein the end portions are aligned to the web portion and extend axially with respect to the annular structure;

delivering the delivery sleeve and valve prosthesis together to the valve annulus; and retracting the delivery sleeve, wherein the end portions of the valve prosthesis have an anchoring condition for anchoring the prosthesis, in which the end portions are shaped asymmetrically and wherein a width of at least one end portion differs from a width of the web portion and extend at an angle to the web portion radially outwardly of the annular structure to provide anchoring of the prosthesis proximally and distally, respectively, of the annulus, and wherein one end portion forms an obtuse angle with the web portion.

\* \* \* \* \*